(12) United States Patent
Knudson et al.

(10) Patent No.: US 9,829,453 B2
(45) Date of Patent: Nov. 28, 2017

(54) APPARATUS FOR ASSESSING THE QUALITY OF MEMBRANE ELECTRODE ASSEMBLIES

(71) Applicant: 3M INNOVATIVE PROPERTIES COMPANY, St. Paul, MN (US)

(72) Inventors: Orlin B. Knudson, Vadnais Heights, MN (US); Daniel M. Pierpont, North St. Paul, MN (US); James F. Poch, Ellsworth, WI (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/483,660

(22) Filed: Apr. 10, 2017

(65) Prior Publication Data

US 2017/0212067 A1     Jul. 27, 2017

Related U.S. Application Data

(63) Continuation of application No. 14/391,549, filed as application No. PCT/US2013/032958 on Mar. 19, 2013, now Pat. No. 9,666,883.

(Continued)

(51) Int. Cl.
*G01F 1/64* (2006.01)
*B29C 65/00* (2006.01)
(Continued)

(52) U.S. Cl.
CPC ......... *G01N 27/02* (2013.01); *G01R 19/0084* (2013.01); *G01R 19/0092* (2013.01);
(Continued)

(58) Field of Classification Search
CPC ...... G01N 27/02; H01M 8/1004; H01M 8/02; H01M 8/04574; H01M 8/04664; H01M 8/04544; G01R 19/0092; G01R 19/0084
(Continued)

(56) References Cited

U.S. PATENT DOCUMENTS

| 5,455,514 A | 10/1995 | Pazda |
| 2005/0183966 A1* | 8/2005 | Kaz ..................... H01M 8/1018 205/775 |

(Continued)

FOREIGN PATENT DOCUMENTS

| CN | 101131410 | 2/2008 |
| CN | 201083802 U | 7/2008 |

(Continued)

OTHER PUBLICATIONS

International Search Report for PCT International Application No. PCT/US2013/032958, dated Jul. 5, 2013, 4 pgs.
Supplementary European Search Report for EP Application No. 13778532; date of completion of the search Nov. 23, 2015 (7 pages).

*Primary Examiner* — Farhana Hoque
(74) *Attorney, Agent, or Firm* — Gregory D. Allen (57) ABSTRACT

An apparatus comprising:
first and second aligned roller pairs each having a nip between the aligned rollers of each aligned roller pair, wherein each of the first and second roller pairs have parallel axes of rotation, wherein each of the first and second aligned roller pairs is configured to electrically excite a portion of the web passed through the nip and to measure an electrical property of the excited web, wherein the first and second aligned roller pairs are configured to electrically excite a portion of the web passed through their respective nips are configured to provide a line of charge parallel to the axes of rotation of the respective roller pairs, and wherein the rollers of the aligned roller pairs are each electrically insulated from each other and from the apparatus; and
a processing unit configured to at least analyze the measured electrical properties.

6 Claims, 5 Drawing Sheets

Related U.S. Application Data (60) Provisional application No. 61/625,220, filed on Apr. 17, 2012.

(51) Int. Cl.
| | | |
|---|---|---|
| *G01N 27/02* | (2006.01) | |
| *H01M 8/1004* | (2016.01) | |
| *H01M 8/02* | (2016.01) | |
| *H01M 8/04537* | (2016.01) | |
| *H01M 8/04664* | (2016.01) | |
| *G01R 19/00* | (2006.01) | |

(52) U.S. Cl.
CPC ......... *H01M 8/02* (2013.01); *H01M 8/04544* (2013.01); *H01M 8/04574* (2013.01); *H01M 8/04664* (2013.01); *H01M 8/1004* (2013.01)

(58) Field of Classification Search
USPC .............................. 324/649; 205/775; 156/64
See application file for complete search history.

(56) References Cited

U.S. PATENT DOCUMENTS

| | | |
|---|---|---|
| 2006/0109003 A1 | 5/2006 | Redko |
| 2007/0104985 A1 | 5/2007 | Tung |
| 2008/0100302 A1 | 5/2008 | Jackson |
| 2010/0108236 A1* | 5/2010 | Berggren ................ H01M 8/00 156/64 |
| 2013/0192750 A1 | 8/2013 | Kiuchi |
| 2014/0239962 A1 | 8/2014 | Oda |
| 2015/0061693 A1 | 5/2015 | Knudson |

FOREIGN PATENT DOCUMENTS

| | | |
|---|---|---|
| JP | 04-069563 | 3/1992 |
| JP | 2004220786 | 8/2004 |
| JP | 2008224560 | 9/2008 |
| JP | 2010061887 | 3/2010 |
| JP | 2013-036768 | 2/2013 |
| KR | 10-2008-0008855 | 1/2008 |

* cited by examiner

APPARATUS FOR ASSESSING THE QUALITY OF MEMBRANE ELECTRODE ASSEMBLIES

CROSS REFERENCE TO RELATED APPLICATIONS

This application is a continuation application of pending prior U.S. application Ser. No. 14/391549, filed Oct. 9, 2014, which is a National Stage Entry of PCT/US2013/032958, filed Mar. 19, 2013, which claims priority from U.S. Provisional Application 61/625220, filed Apr. 17, 2012, the disclosures of which are incorporated by reference in their entireties herein.

BACKGROUND

Methods for quality control testing of fuel cell membrane electrode assemblies (MEAs) include those utilizing stand-alone fixtures to measure discrete MEA part resistance on a non-continuous, "one at a time" basis. The test is run by a system that compresses a single MEA between two conductive plates and applies a voltage to the discrete MEA. The procedure is relatively time consuming and typically requires more than one minute per MEA, as well as adds additional handling to the relatively fragile and expensive MEA. It is desirable to reduce the number of handling steps, and therefore reduce the potential debris or damage occurring to an MEA. As new methods evolve for manufacturing MEAs in a continuous process it would also be advantageous to run quality control measures in line with the manufacture.

SUMMARY

In one aspect, the present disclosure describes an apparatus comprising:
  first and second aligned roller pairs each having a nip between the rollers of a pair of rollers, wherein each of the first and second roller pairs is configured to electrically excite a web passed through the nip and to measure an electrical property of the excited web, and wherein the rollers are each electrically insulated from each other and from the apparatus; and
  a processing unit configured to at least analyze the measured electrical properties.

In another aspect, the present disclosure describes a method for assessing the quality of membrane electrode assemblies, the method comprising:
  providing a web comprising a plurality of distinct membrane electrode assemblies each having a thickness;
  applying a first voltage across the thickness of a first membrane electrode assembly of the web thereby providing a first charge to the first membrane electrode assembly;
  determining a first electrical figure of merit of the first charged membrane electrode assembly at a first period of time;
  after the first period of time applying a second voltage across the thickness of the first membrane electrode assembly thereby providing a second charge to the first membrane electrode assembly;
  determining a second electrical figure of merit of the first charged membrane electrode assembly at a second, later period of time; and
  calculating a total electrical figure of merit using the first and second electrical figure of merits; and
  comparing the total electrical figure of merit to a predetermined quality value to assess the quality of the membrane electrode assembly. For a second (and additional) membrane electrodeassembly the method further comprises:
  applying a first voltage across the thickness of a second membrane electrode assembly thereby providing a first charge to the second membrane electrode assembly;
  determining a first electrical figure of merit of a second charged membrane electrode assembly at a first period of time;
  after the a first point in time applying a second voltage across the thickness of the second membrane electrode assembly thereby providing a second charge to the second membrane electrode assembly;
  determining a second electrical figure of merit of the second charged membrane electrode assembly at a second, later period of time; and
  calculating a total electrical figure of merit using the first and second electrical figure of merits; and
  comparing the total electrical figure of merit to a predetermined quality value to assess the quality of the membrane electrode assembly.

In another aspect, the present disclosure describes a method for assessing the quality of at least one membrane electrode assembly, the method comprising:
  providing a first membrane electrode assembly having a thickness;
  applying a first voltage across the thickness of the first membrane electrode assembly when passing the first membrane electrode assembly through a nip of a first pair of rollers thereby providing a first charge to the first membrane electrode assembly;
  determining a first electrical figure of merit of the first charged membrane electrode assembly at a first period of time;
  after the first period of time applying a second voltage across the thickness of the first membrane electrode assembly when passing the first membrane electrode assembly through a nip of a second pair of rollers thereby providing a second charge to the first membrane electrode assembly;
  determining a second electrical figure of merit of the second charged membrane electrode assembly at a second, later period of time; and
  calculating a total electrical figure of merit using the first and second electrical figure of merits; and
  comparing the total electrical figure of merit to a predetermined quality value to assess the quality of the membrane electrode assembly. For a second (and additional) membrane electrode assembly the method further comprises:
  applying a first voltage across the thickness of a second membrane electrode assembly thereby providing a first charge to the second membrane electrode assembly;
  determining a first electrical figure of merit of a second charged membrane electrode assembly at a first period of time;
  after the a first point in time applying a second voltage across the thickness of the second membrane electrode assembly thereby providing a second charge to the second membrane electrode assembly;
  determining a second electrical figure of merit of the second charged membrane electrode assembly at a second, later period of time; and
  calculating a total electrical figure of merit using the first and second electrical figure of merits; and comparing the total electrical figure of merit to a predetermined quality value to assess the quality of the membrane electrode assembly.

In another aspect, the present disclosure describes a method for assessing the quality of at least one membrane electrode assembly, the method comprising:

providing a first membrane electrode assembly having a thickness;

applying a first voltage across the thickness of the first membrane electrode assembly thereby providing a first line of charge to the first membrane electrode assembly;

determining a first electrical figure of merit of the first charged membrane electrode assembly at a first period of time;

after the first period of time applying a second voltage across the thickness of the first membrane electrode assembly thereby providing a second line of charge to the first membrane electrode assembly;

determining a second electrical figure of merit of the second charged membrane electrode assembly at a second, later period of time; and calculating a total electrical figure of merit using the first and second electrical figure of merits; and comparing the total electrical figure of merit to a predetermined quality value to assess the quality of the membrane electrode assembly. For a second (and additional) membrane electrode assembly the method further comprises:

applying a first voltage across the thickness of a second membrane electrode assembly thereby providing a first charge to the second membrane electrode assembly;

determining a first electrical figure of merit of a second charged membrane electrode assembly at a first period of time;

after the a first point in time applying a second voltage across the thickness of the second membrane electrode assembly thereby providing a second charge to the second membrane electrode assembly;

determining a second electrical figure of merit of the second charged membrane electrode assembly at a second, later period of time; and calculating a total electrical figure of merit using the first and second electrical figure of merits; and comparing the total electrical figure of merit to a predetermined quality value to assess the quality of the membrane electrode assembly.

In this application:

"Electrical figure of merit" refers to a set of measurements or calculations that are used to characterize an electrical aspect of the quality of the fuel cell membrane electrode assembly.

"Membrane electrode assembly" refers to a layered sandwich of fuel cell materials comprising a membrane, anode and cathode electrode layers and gas diffusion layers.

Advantages of methods described herein for assessing the quality of membrane electrode assemblies include increased part throughput rates, reduction in the probability of part damage, and validated efficacy as compared to a stand alone, single part tester. Methods described herein for assessing the quality of MEAs are considered to be, or generally to be, non-destructive tests. The method can be useful, for example, to validate data that has been directly correlated between resistance test values of MEAs to actual stack test data. This correlation may assist in predicting MEA quality (e.g., acceptable or not acceptable) before assembly into a stack where it is fixed and extremely expensive to replace.

Since a stack of MEAs is only as good as the worst MEA, the ability to identify and remove poor quality or defective parts advantageously affects the robustness and durability of the stack.

DETAILED DESCRIPTION

Figure 1:
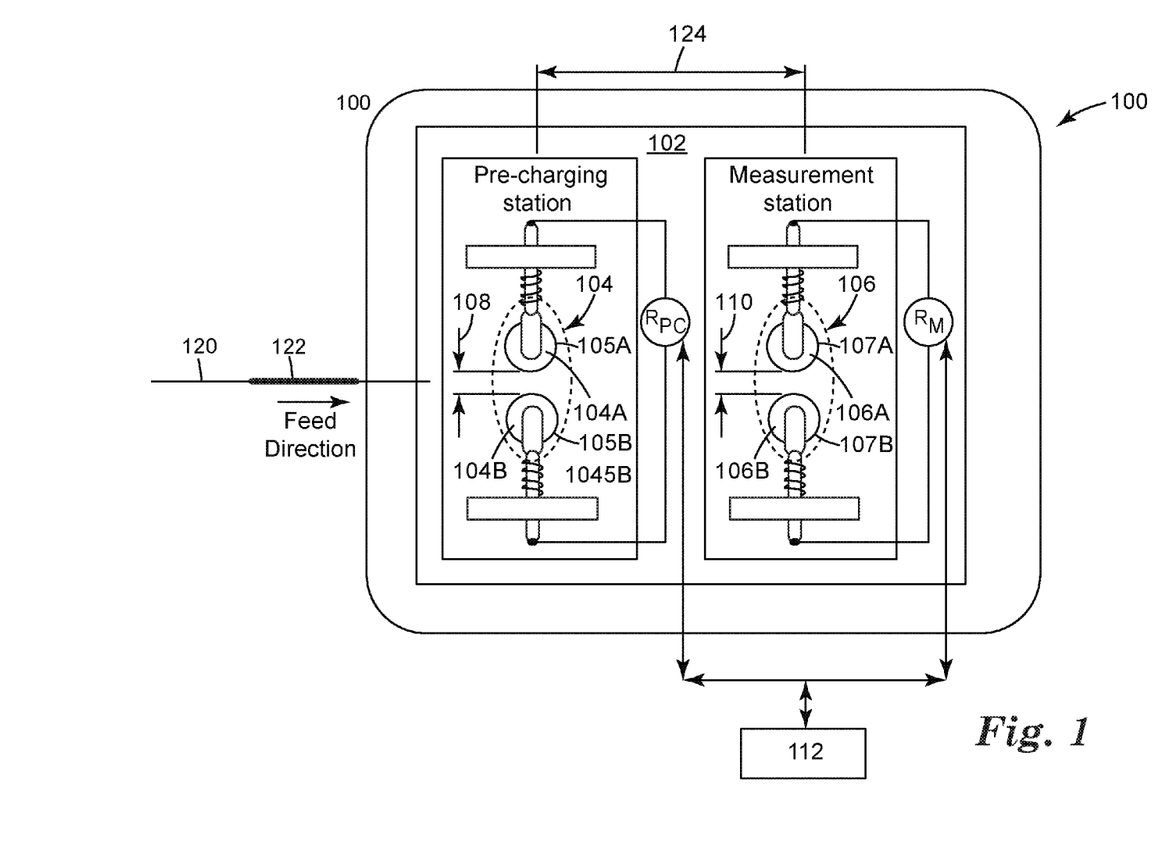
FIG. 1 is a schematic of an exemplary apparatus described herein useful for assessing the quality of at least one membrane electrode assembly.
Figure 2:
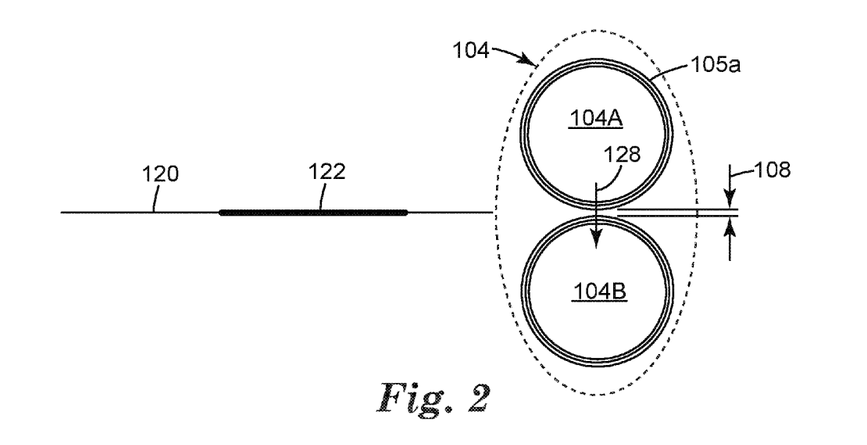
FIG. 2 is a more detailed schematic of a roller pair from FIG. 1.

Referring to FIG. 1, an exemplary apparatus described herein is shown as being useful for assessing the quality of membrane electrode assemblies (MEAs). Apparatus 100 has frame 102 with first and second aligned roller pairs 104, 106 each having nip 108, 110 between roller pairs 104, 106 of rollers Roller pairs 104, 106 are each configured to electrically excite a web (120) with that membrane electrode assemblies (122) passes through nips 108, 110. As shown outer surfaces 105a, 105b, 107a, 107b of the rollers may comprise gold. The roller pairs may are separated a distance 124. The desired electrical property of the excited membrane electrode assembly is measured or determined from at least one measurement from a sensor(s) not shown that is part of or near roller 104A or 104B and 106A or 106B. Processing unit (e.g., a computer equipped with communication and data acquisition software and mathematical analysis capability) 112 is configured to at least analyze the measured electrical properties. Alternative measurement systems and processing units include a dedicated micro-controller controlling an analog voltage or current with an analog to digital converter detecting the resulting current or voltage, and with associated memory, communications capability and a "pass/fail" output indicator.

The components of the apparatus can be made from materials known in the art, and which will be apparent to one skilled in the art after reading the instant disclosure, including the Examples, below. For example, the frame, rollers and associated hardware of the apparatus can be made of metal (e.g., aluminum or steel). In some embodiments, outer surfaces of the rollers for contacting a web or membrane electrode assembly may comprise at least one of one of chromium, gold, nickel, palladium, rhodium, or silver. While gold typically provides an excellent electrical conductance and contact resistance to the MEA, other materials may improve the robustness of the outer surface of the roller. Typically, the gap spacing and pressure exerted on the MEA is sufficient to compress the compressible gas diffusion layer to provide good electrical contact between the MEA and the rollers. In some embodiments, the desired pressure exerted on the MEA is in a range from about 35 kPa to 275 kPa (5 psi to 40 psi) (in some embodiments, 140 kPa to 210 kPa (20 psi to 30 psi)), although the desired pressure for a particular MEA and assembly arrangement may be outside of these ranges.

The nip(s) can have fixed gaps or apply a fixed pressure. Nip gaps 108, 110 are determined by the thickness of the MEA. Alternatively, for example, a nip pressure can be used to set a constant load across the nips.

Typically, the roller pairs are configured to provide a line of electrical charge parallel to the axes of rotation of the respective roller pair. The line of charge can be provided by the nip of the rotating roller pair wherein charge is delivered from one roller through the MEA to the second roller as the active region of an MEA passes through the nip. Using this method, a discrete MEA part, or a plurality of MEA parts on a continuous web can be evaluated. Typically, each roller is electrically insulated from each other and from the apparatus. Isolation of the rollers from the chassis and each other parts of the apparatus provides a more desired electrical measurement. While not wanting to be bound by theory, it is believed that this isolation separates the small DC measurement signals and the measurement return signal from the larger chassis currents (electrical noise) that may be present due to motor drive and its associated control. This isolation can be provided, for example, by combinations of electrically insulating bearings, isolating motor shafts, electrically isolating an outside covering of the roller from the core of the roller, etc.

In some embodiments, the line of charge parallel to the axes of rotation of a respective roller pair independently has a length of at least 15 cm (in some embodiments, in a range from 15 cm to 75 cm, or even 25 cm to 50 cm). Typically, each membrane electrode assembly has a width parallel to the respective axes of the rollers, and each of the lines of charge is greater than the widths of the membrane electrode assembly.

In some embodiments, the distance between a pair of rollers is at least 25 cm (in some embodiments, in a range from 25 cm to 50 cm). The range of separation is necessary to accommodate different part sizes. Different applications may benefit from different part sizes.

In some embodiments, there may be a third, or, fourth, or more pair of rollers.

Typically, voltages or electrical current are applied across the rolls of a set of rollers. The first applied voltage or electrical current is not less (including in some embodiments greater) than the second voltage or electrical current, however, in some embodiments, the first applied voltage or electrical current is not greater than the second voltage or electrical current. The first voltage or electrical current electrical current can be applied to a roller on the first roller pair using conventional equipment such as that available from Keithley Instruments, Cleveland, Ohio, under the trade designation "KEITHLEY SERIES 2400 DIGITAL SOURCEMETER INSTRUMENT"). The other roller of the first pair is connected to the return circuit on the voltage or electrical current applying equipment. This measurement circuit is electrically isolated from the chassis of the measurement system.

In some embodiments, the electrical property, for example, an electrical figure of merit is voltage, current, resistance and/or charge. In some embodiments, the electrical property measured is a (time indexed) array of values (e.g., electrical voltage and electrical current) from which other figures of merit such as electrical charge and electrical resistance can be calculated or otherwise determined. The selection of the figure(s) of merit to use is dependent upon the type of MEA.

It is also within the scope of the present disclosure to distinguish between desired and undesired MEAs by applying a higher voltage across the measurement nip than the voltage across the pre-charge nip making sure not to overexcite the MEA.

Typically, the difference in time between the first and second periods of time is not greater than 5 seconds (in a range from 0.25 second to 5 seconds), although shorter or longer times are also useful, and may depend, for example, on the particular process or quality needs, materials being evaluated, nip spacing, nip pressure, speed of the MEA(s), etc.

Advantages of methods described herein for assessing the quality of membrane electrode assemblies include increased part throughput rates, reduction in the probability of part damage, and validated efficacy as compared to a stand alone, discrete part tester. Methods described herein for assessing the quality of MEAs are generally considered to be non-destructive tests. The method can be useful, for example, to validate that data has been directly correlated between resistance test values of MEAs and actual stack test data. This correlation may assist in predicting MEA quality (e.g., acceptable or not acceptable) before assembly into a stack where it is fixed and extremely expensive to replace. Since a stack of MEAs is only as good as the worst MEAs the ability to identify and remove unacceptable parts can advantageously affect the robustness and durability of the stack.

Exemplary Embodiments

1A. An apparatus comprising:
   first and second aligned roller pairs each having a nip between the rollers of a pair of rollers, wherein each of the first and second roller pairs is configured to electrically excite a portion of the web passed through the nip and to measure an electrical property of the excited web, and wherein the rollers are each electrically insulated from each other and from the apparatus; and
   a processing unit configured to at least analyze the measured electrical properties.

2A. The apparatus of Embodiment 1A, wherein the nip has a fixed gap.

3A. The apparatus of Embodiment 1A, wherein the nip applies a fixed pressure.

4A. The apparatus of any preceding Embodiment A, wherein the first and second roller pairs are at least 10 cm (in some embodiments, at least 15 cm, 20 cm, or even at least 25 cm; in some embodiments, in a range from 10 cm to 50 cm, 15 cm to 50 cm, or even 25 cm to 50 cm) apart.

5A. The apparatus of any preceding Embodiment A, wherein each of the first and second roller pairs have parallel axes of rotation, and wherein the first and second roller pairs are configured to electrically excite a portion of the web passed through the nip are configured to provide a line of charge parallel to the axes of rotation of the respective roller pairs.

6A. The apparatus of Embodiment 5A, wherein the line of charge parallel to the axes of rotation of the respective roller pairs independently have a length of at least 15 cm (in some embodiments, in a range from 15 cm to 75 cm, or even 25 cm to 50 cm).

7A. The apparatus of any preceding Embodiment A, wherein the rollers have outer surfaces that for contacting a web that comprise at least one of chromium, gold, nickel, palladium, rhodium, or silver.

8A. The apparatus of any preceding Embodiment A, wherein the electrical property measured is an array of values.

9A. The apparatus of any preceding Embodiment A, wherein the electrical property measured is voltage.

10A. The apparatus of any of Embodiments 1A to 8A, wherein the electrical property measured is current.

11A. The apparatus of Embodiments 1A to 8A, wherein the electrical property measured is both voltage and current.

1B. A method for assessing the quality of membrane electrode assemblies, the method comprising:

providing web comprising a plurality of distinct membrane electrode assemblies each having a thickness;

applying a first voltage across the thickness of a first membrane electrode assembly of the web thereby providing a first charge to the first membrane electrode assembly;

determining a first electrical figure of merit of the first charged membrane electrode assembly at a first period of time;

after the first period of time applying a second voltage across the thickness of the first membrane electrode assembly thereby providing a second charge to the first membrane electrode assembly;

determining a second electrical figure of merit of the first charged membrane electrode assembly at a second, later period of time;

calculating a total electrical figure of merit using the first and second electrical figure of merits; and comparing the total electrical figure of merit to a predetermined quality value to assess the quality of the membrane electrode assembly.

2B. The method of Embodiment 1B, wherein the first voltage is applied across the thickness of the first membrane electrode assembly when passing the web through a nip of a first pair of rollers.

3B. The apparatus of Embodiment 2B, wherein the nip has a fixed gap.

4B. The apparatus of Embodiment 2B, wherein the nip applies a fixed pressure.

5B. The method of any preceding Embodiment B, wherein the second voltage is applied across the thickness of the first membrane electrode assembly when passing the web through a nip of a second pair of rollers.

6B. The method of Embodiment 4B, wherein each of the first and second roller pairs have parallel axes of rotation, and wherein each of the charges is applied in a line parallel to the axes of rotation of the respective roller pairs.

7B. The method of Embodiment 4B, wherein the membrane electrode assemblies each have width parallel to the respective axes of the rollers, and wherein each of the lines of charge are greater than the widths of the membrane electrode assemblies.

8B. The method of any either Embodiment 6B or 7B, wherein the lines of charge independently have a length of at least 15 cm (in some embodiments, in a range from 15 cm to 75 cm, or even 25 cm to 50 cm).

9B. The apparatus of any of Embodiments 6B to 8B, wherein the first and second roller pairs are at least 25 cm (in some embodiments, in a range from 25 cm to 50 cm) apart.

10B. The method of any of Embodiments 6B to 9B, wherein the rollers have outer surfaces contacting the membrane electrode assemblies, and wherein the outer surfaces comprise one of chromium, gold, nickel, palladium, rhodium, or silver.

11B. The method of any preceding B Embodiments further comprising:

applying a first voltage across the thickness of a second membrane electrode assembly thereby providing a first charge to the second membrane electrode assembly;

determining a first electrical figure of merit of a second charged membrane electrode assembly at a first period of time;

after the a first point in time applying a second voltage across the thickness of the second membrane electrode assembly thereby providing a second charge to the second membrane electrode assembly;

determining a second electrical figure of merit of the second charged membrane electrode assembly at a second, later period of time; and calculating a total electrical figure of merit using the first and second electrical figure of merits; and comparing the total electrical figure of merit to a predetermined quality value to assess the quality of the membrane electrode assembly.

12B. The method of any preceding Embodiment B, wherein the first electrical figure of merit is an array of values determined during the first period of time, and wherein the second electrical figure of merit is an array of values determined during the second period of time.

13B. The method of any preceding Embodiment B, wherein the first electrical figure of merit is voltage and the second electrical figure of merit is electrical voltage.

14B. The method of any preceding 1B to 12B Embodiments, wherein the first electrical figure of merit is current and the second electrical figure of merit is current.

15B. The apparatus of Embodiments 1B to 12B, wherein the first electrical figure of merit is both voltage and current and the second electrical figure of merit both voltage and current.

16B. The method of any preceding Embodiment B, wherein the difference in time between the first and second periods of time is not greater than 5 seconds (in a range from 0.25 second to 5 seconds).

17B. The method of any preceding Embodiment B, wherein the first applied voltage is not less than the second voltage.

18B. The method of any of Embodiments 1B to 16B, wherein the first applied voltage is not greater than the second voltage.

1C. A method for assessing the quality of at least one membrane electrode assembly, the method comprising:

providing a first membrane electrode assembly having a thickness;

applying a first voltage across the thickness of the first membrane electrode assembly when passing the first membrane electrode assembly through a nip of a first pair of rollers thereby providing a first charge to the first membrane electrode assembly;

determining a first electrical figure of merit of the first charged membrane electrode assembly at a first period of time;

after the first period of time applying a second voltage across the thickness of the first membrane electrode assembly when passing the first membrane electrode assembly through a nip of a second pair of rollers thereby providing a second charge to the first membrane electrode assembly;

determining a second electrical figure of merit of the second charged membrane electrode assembly at a second, later period of time; and calculating a total electrical figure of merit using the first and second electrical figure of merits; and comparing the total electrical figure of merit to a predetermined quality value to assess the quality of the membrane electrode assembly.

2C. The apparatus of Embodiment 1C, wherein the nip has a fixed gap.

3C. The apparatus of Embodiment 1C, wherein the nip applies a fixed pressure.

4C. The method of any preceding Embodiment C, wherein each of the first and second roller pairs have parallel axes of rotation, and wherein each of the charges is applied in a line parallel to the axes of rotation of the respective roller pairs.

5C. The method of Embodiment 4C, wherein the membrane electrode assemblies each have width parallel to the respective axes of the rollers, and wherein each of the lines of charge is greater than the widths of the membrane electrode assemblies.

6C. The method of any either Embodiment 4C or 5C, wherein the lines of charge independently have a length of at least 15 cm (in some embodiments, in a range from 15 cm to 75 cm, or even 25 cm to 50 cm).

7C. The apparatus of any preceding Embodiment C, wherein the first and second roller pairs are at least 25 cm (in some embodiments, in a range from 25 cm to 50 cm) apart.

8C. The method of any preceding Embodiment C, wherein the rollers have outer surfaces contacting the first membrane electrode assembly, and wherein said outer surfaces comprise one of chromium, gold, nickel, palladium, rhodium, or silver.

9C. The method of any preceding C Embodiments further comprising:
applying a first voltage across the thickness of a second membrane electrode assembly thereby providing a first charge to the second membrane electrode assembly;
determining a first electrical figure of merit of a second charged membrane electrode assembly at a first period of time;
after a first point in time applying a second voltage across the thickness of the second membrane electrode assembly thereby providing a second charge to the second membrane electrode assembly;
determining a second electrical figure of merit of the second charged membrane electrode assembly at a second, later period of time; and
calculating a total electrical figure of merit using the first and second electrical figures of merit; and
comparing the total electrical figure of merit to a predetermined quality value to assess the quality of the second membrane electrode assembly.

10C. The method of any preceding Embodiment C, wherein the first electrical figure of merit is an array of values determined during the first period of time, and wherein the second electrical figure of merit is an array of values determined during the second period of time.

11C. The method of any preceding Embodiment C, wherein the first electrical figure of merit is voltage and the second electrical figure of merit is voltage.

12C. The method of any 1C to 10C Embodiments, wherein the first electrical figure of merit is current and the second electrical figure of merit is current.

13C. The apparatus of Embodiments 1C to 10C, wherein the first electrical figure of merit is both voltage and current and the second electrical figure of merit is both voltage and current.

14C. The method of any preceding Embodiment C, wherein the difference in time between the first and second periods of time is not greater than 5 seconds (in a range from 0.25 second to 5 seconds).

15C. The method of any preceding Embodiment C, wherein the first applied voltage is not less than the second voltage.

16C. The method of any Embodiments 1C to 14C, wherein the first applied voltage is not greater than the second voltage.

1D. A method for assessing the quality of at least one membrane electrode assembly, the method comprising:
providing a first membrane electrode assembly having a thickness;
applying a first voltage across the thickness of the first membrane electrode assembly thereby providing a first line of charge to the first membrane electrode assembly;
determining a first electrical figure of merit of the first charged membrane electrode assembly at a first period of time;
after the first period of time applying a second voltage across the thickness of the first membrane electrode assembly thereby providing a second line of charge to the first membrane electrode assembly;
determining a second electrical figure of merit of the second charged membrane electrode assembly at a second, later period of time; and
calculating a total electrical figure of merit using the first and second electrical figure of merits; and
comparing the total electrical figure of merit to a predetermined quality value to assess the quality of the membrane electrode assembly.

2D. The apparatus of Embodiment 1D, wherein the nip has a fixed gap.

3D. The apparatus of Embodiment 1D, wherein the nip applies a fixed pressure.

4D. The method of any either of Embodiments 2D or 3D, wherein the line of charge is provided by applying the second voltage across the thickness of the second membrane electrode assembly when passing the first membrane electrode assembly through a nip of a second pair of rollers.

5D. The method of Embodiment 4D, wherein the first membrane electrode assembly has a width parallel to the respective axes of the rollers, and wherein each of the lines of charge are greater than the widths of the membrane electrode assemblies.

6D. The method of any preceding Embodiment D, wherein the lines of charge independently have a length of at least 15 cm (in some embodiments, in a range from 15 cm to 75 cm, or even 25 cm to 50 cm).

7D. The apparatus of any preceding Embodiment D, wherein the first and second roller pairs are at least 25 cm (in some embodiments, in a range from 25 cm to 50 cm) apart.

8D. The method of any preceding Embodiment D, wherein the rollers have outer surfaces contacting the first membrane electrode assembly, and wherein the outer surfaces comprise one of chromium, gold, nickel, palladium, rhodium, or silver.

9D. The method of any preceding Embodiment D further comprising:
applying a first voltage across the thickness of a second membrane electrode assembly thereby providing a first charge to the second membrane electrode assembly;

determining a first electrical figure of merit of a second charged membrane electrode assembly at a first period of time;

after the a first point in time applying a second voltage across the thickness of the second membrane electrode assembly thereby providing a second charge to the second membrane electrode assembly;

determining a second electrical figure of merit of the second charged membrane electrode assembly at a second, later period of time; and calculating a total electrical figure of merit using the first and second electrical figure of merits; and comparing the total electrical figure of merit to a predetermined quality value to assess the quality of the membrane electrode assembly.

10D. The method of any preceding D Embodiments, wherein the first electrical figure of merit is an array of values determined during the first period of time, and wherein the second electrical figure of merit is an array of values determined during the second period of time.

11D. The method of any preceding D Embodiments, wherein the first electrical figure of merit is voltage and the second electrical figure of merit is voltage.

12D. The method of any preceding 1D to 10D Embodiments, wherein the first electrical figure of merit is current and the second electrical figure of merit is current.

13D. The method of Embodiments 1D to 10D, wherein the first electrical figure of merit is both voltage and current and the second electrical figure of merit both voltage and current.

14D. The method of any preceding D Embodiments, wherein the difference in time between the first and second periods of time is not greater than 5 seconds (in a range from 0.25 second to 5 seconds).

15D. The method of any preceding D Embodiments, wherein the first applied voltage is not less than the second voltage.

16D. The method of any of Embodiments 1D to 14D, wherein the first applied voltage is not greater than the second voltage.

Advantages and embodiments of this invention are further illustrated by the following examples, but the particular materials and amounts thereof recited in these examples, as well as other conditions and details, should not be construed to unduly limit this invention. All parts and percentages are by weight unless otherwise indicated.

EXAMPLES

General Method of Testing MEAs

The MEA samples to be tested were manually fed to testing apparatus 100 as generally shown in FIG. 1 one at a time. Apparatus 100 had frame 102 with first and second aligned roller pairs 104, 106 each having nip 108, 110 between roller pairs 104, 106 of rollers Roller pairs 104, 106 were each configured to electrically excite a web (120) with that membrane electrode assemblies (122) passed through nips 108, 110. As shown outer surfaces 105a, 105b, 107a, 107b of the rollers comprise gold. The roller pairs were separated a distance 124 of 33 cm. The desired electrical property of the excited membrane electrode assembly was measured or determined from at least one measurement from a sensor(s) not shown that is part of or near roller 104A or 104B and 106A or 106B. Processing unit (e.g., a computer equipped with communication and data acquisition software and mathematical analysis capability) 112 is configured to at least analyze the measured electrical properties.

The apparatus as generally shown in FIG. 1 was turned on, setting two pairs of rollers in rotation. The first pair of rollers formed the pre-charge nip and the second pair of rollers formed the measurement nip. Then the data acquisition system controlled by data acquisition software (written using software obtained under the trade designation "LABVIEW" from National Instruments Corporation, Austin, Tex.) was turned on. The data acquisition software was used to communicate with the data acquisition system in near real time, and controlled the component instruments, collected, manipulated (i.e., performed mathematical operations), and saved the data. Specifically, the data acquisition software was used to control the power source (obtained under the trade designation "KEITHLEY MODEL 2400 SOURCE METER" from Keithley Instruments, Inc., Cleveland, Ohio), set a predetermined potential across the pre-charge and measurement nips, and examined the data from the instruments. When the resistance suddenly decreases as a MEA to be tested was fed indicating that a test sample was detected, the data acquisition software started recording current and voltage data versus time. The data acquisition software, then computed the desired figures of merit data for the sample being tested and saved the data.

When the MEA to be tested, which had no stored energy, was fed to the nip of the pre-charge rollers, the nip grabbed and carried the MEA through the nip. As the MEA passed through the nip, the system sensed the resistance, $R_{PC}$ (i.e., the sudden change in resistance) and started collecting, manipulating and saving the data. The voltage, $V_{PC}$, and current, $I_{PC}$, were measured and resistance, $R_{PC}$, and charge, $Q_{PC}$, were calculated and saved. The measured and calculated data were saved as a function of time (i.e., sample, n), so that each measured and calculated data was a sequence of numbers, $V_{PC}\{n\}$, $I_{PC}\{n\}$ $R_{PC}\{n\}$, $Q_{PC}\{n\}$.

When the active region of the MEA left the pre-charge nip, the resistance returned to a high level. As the MEA entered in to and moved through the second measurement nip, again the resistance dropped from high to low, triggering the data collection versus time. When the MEA was in the measurement nip the voltage, $V_M$, current, $I_M$, was measured and resistance, $R_M$, and charge, $Q_M$ were calculated and saved as a sequence of numbers, $V_M\{n\}$, $I_M\{n\}$ $R_M\{n\}$, $Q_M\{n\}$. After the MEA left the measurement nip, various figures of merit are calculated, and the system provided an "acceptable" or "unacceptable" signal against pre-defined figure of merit threshold levels.

During the test the potential applied across the pre-charge and measurement nips may have been the same or different, and is noted as such in the particular Example. Typically the potential applied across the pre-charge nip is the same as the potential applied across the measurement nip, and is noted as such in the particular Example. Alternatively, the potential applied across the pre-charge nip may be greater than the potential applied across the measurement nip, although the reverse may also be useful. Generally, the separation between the "acceptable" and "unacceptable" MEAs could be enhanced by increasing the difference in voltage applied across the pre-charge and measurements nips. However, further separation between the "acceptable" and "unacceptable" MEAs could be accomplished, for example, by using applied voltages of 0.3V and 0.1V (or even 0.3V and 0.01V) across the pre-charge and measurements nips, respectively. However, care must be taken not to overexcite an MEA sample during testing.

Another way of further separating the "acceptable" and "unacceptable" MEAs is to use absolute values of, for example, resistance. In some embodiments, a figure of merit array or graphical values could be used as an input to a function which produces a scalar figure of merit. This scalar figure of merit could be used to distinguish between desired and undesired MEAs.

Useful figures of merit include, for example, resistance at a specified time, t, or sample, n, resistance difference between pre-charge and measurement nips, at a specified time, t, or sample, n, integral of the resistance difference, current difference between pre-charge and measurement nips, charge difference between pre-charge and measurement nips, resistance summation difference between pre-charge and measurement nips, current summation difference between pre-charge and measurement nips, charge summation difference between pre-charge and measurement nips or combination of any number of them. Other useful and applicable figures of merit may be defined and used by the persons skilled in the art.

For example, it is believed that during testing of an MEA, when the voltage was applied, the MEA's capacitance charged until it leveled off and a value for the leakage current could be measured and the resistance, in ohms, of the MEA calculated. If the MEA resistance was too low, this implied that there could be some carbon fibers or other metal poking through and shorting the membrane or there was a defect or thin spot in the membrane material. Both of these circumstances are known to lead to early failure of an MEA. Generally, by setting an acceptable MEA resistance threshold (according to a customer requirement or size of the MEA) and comparing the resistance of the tested MEA to the threshold value made it possible to distinguish "acceptable" (i.e., MEA resistance was higher than the threshold) and "unacceptable" (i.e., MEA resistance was lower than the threshold) MEAs.

Example 1

Figure 3:
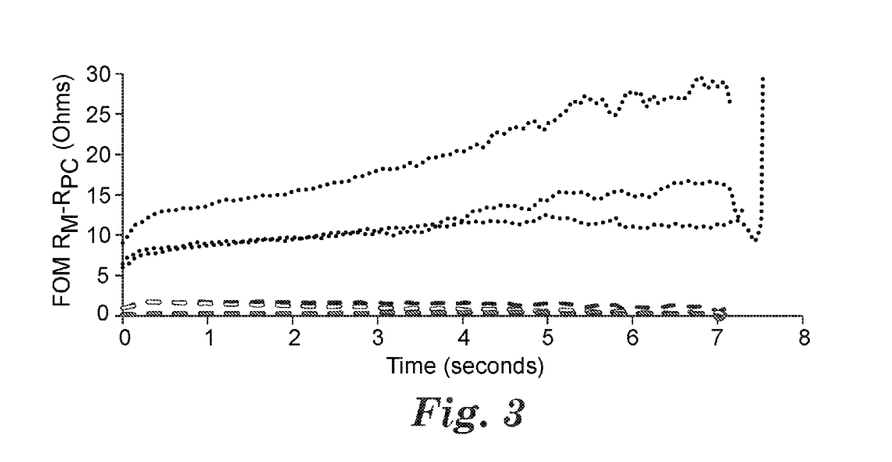
FIG. 3 is a graph of data for representative MEA samples of Example 1.

Twenty-five discrete MEA samples were tested according to the General Method of Testing MEAs. MEA samples were prepared by methods commonly known in the art. The MEAs were about 15 centimeters by about 20 centimeters in dimension and they were about 0.45 millimeter thick. The MEA samples were manually fed to the testing apparatus one at a time. The voltage applied across the pre-charge and measurements nips were 0.3V and 0.3V, respectively. The figure of merit used to separate the "acceptable" and the "unacceptable" MEAs was resistance difference comparison ($FOM_{subtraction}\{n\}$ in units of ohms) defined as:

$$FOM_{subtraction}\{n\}=f(R_M, R_{PC})=R_M\{n\}-R_{PC}\{n\}$$

wherein $R_M\{n\}$ and $R_{PC}\{n\}$ were the measured and pre-charge resistance for the nth data point in the arrays, respectively, for the MEA being tested. Graphical representation of the $FOM_{subtraction}\{n\}$ data for three "acceptable" (represented by dotted lines) and three "unacceptable" (represented by broken lines) MEAs are given in FIG. 3.

Example 2

Figure 4:
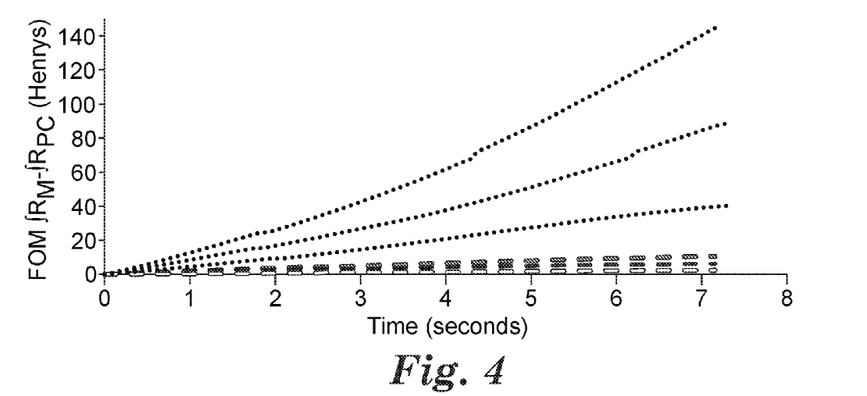
FIG. 4 is a graph of data for representative MEA samples of Example 2.

Twenty-six discrete MEA samples were prepared and tested as described for Example 1, except the figure of merit used to separate the "acceptable" and the "unacceptable" MEAs was resistance difference integration ($FOM_{integration\_of\_difference}\{n\}$ in units of Henrys) defined as:

$$FOM_{integration\_of\_difference} =$$
$$f(R_m, R_{PC}, T) = \sum_{n=0}^{k} R_m\{n\}T_{R_M}\{n\} - \sum_{n=0}^{j} R_{PC}\{n\}\Delta T_{R_{PC}}\{n\}$$

wherein $R_M\{n\}$ and $R_{PC}\{n\}$ were the measured and pre-charge resistance for the nth data point in the arrays, respectively, for the MEA being tested and $\Delta T_{RM}\{n\}$ and $\Delta T_{RPC}\{n\}$ was the time for the measurement nip and the pre-charge nip, respectively, for the nth sample. Graphical representation of the $FOM_{integration\_of\_difference}\{n\}$ data for three "acceptable" (represented by dotted lines) and three "unacceptable" (represented by broken lines) MEAs are given in FIG. 4.

Example 3

Figure 5:
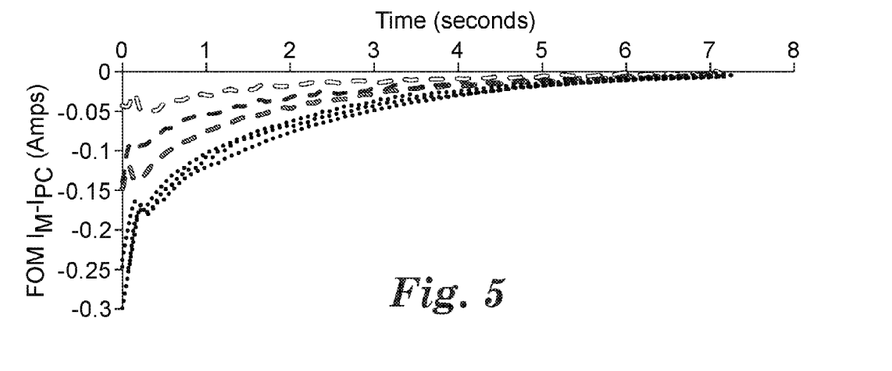
FIG. 5 is a graph of data for representative MEA samples of Example 3.

Twenty-four discrete MEA samples were prepared and tested as described for Example 1, except the figure of merit used to separate the "acceptable" and the "unacceptable" MEAs was current difference comparison ($FOM_{subtraction\ of\ current}\{n\}$ in units of amps) defined as:

$$FOM_{subtraction\ of\ current}\{n\}=f(I_M, I_{PC})=I_M\{n\}-I_{PC}\{n\}$$

wherein $I_M\{n\}$ and $I_{PC}\{n\}$ were the measured and pre-charge current for the nth data point in the arrays, respectively, for the MEA being tested. Graphical representation of the $FOM_{subtraction\ of\ current}\{n\}$ data for three "acceptable" (represented by dotted lines) and three "unacceptable" (represented by broken lines) MEAs are given in FIG. 5.

Example 4

Figure 6:
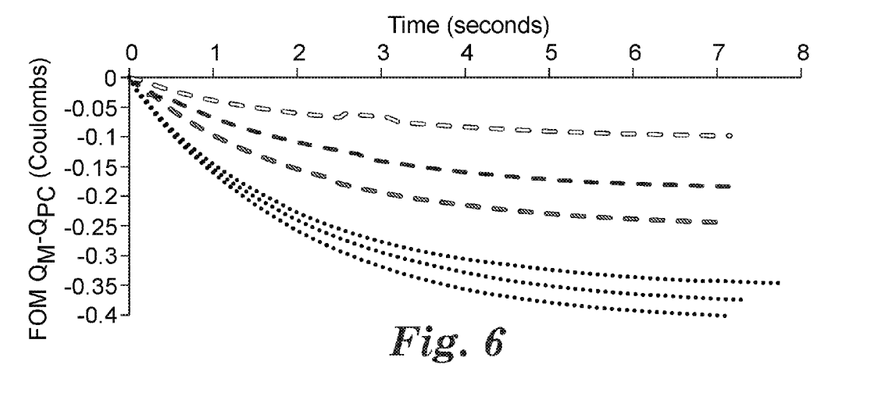
FIG. 6 is a graph of data for representative MEA samples of Example 4.

Twenty-six discrete MEA samples were prepared and tested as described for Example 1, except the figure of merit used to separate the "acceptable" and the "unacceptable" MEAs was charge difference comparison ($FOM_{subtraction\ of\ charge}\{n\}$ in units of coulombs) defined as:

$$FOM_{subtraction\ of\ charge}\{n\}=f(Q_M, Q_{PC})=Q_M\{n\}-Q_{PC}\{n\}$$

wherein $Q_M\{n\}$ and $Q_{PC}\{n\}$ were the measured and pre-charge charge for the nth data point in the arrays, respectively, for the MEA being tested. Graphical representation of the $FOM_{subtraction\ of\ charge}\{n\}$ data for three "acceptable" (represented by dotted lines) and three "unacceptable" (represented by broken lines) MEAs are given in FIG. 6.

Example 5

Figure 7:
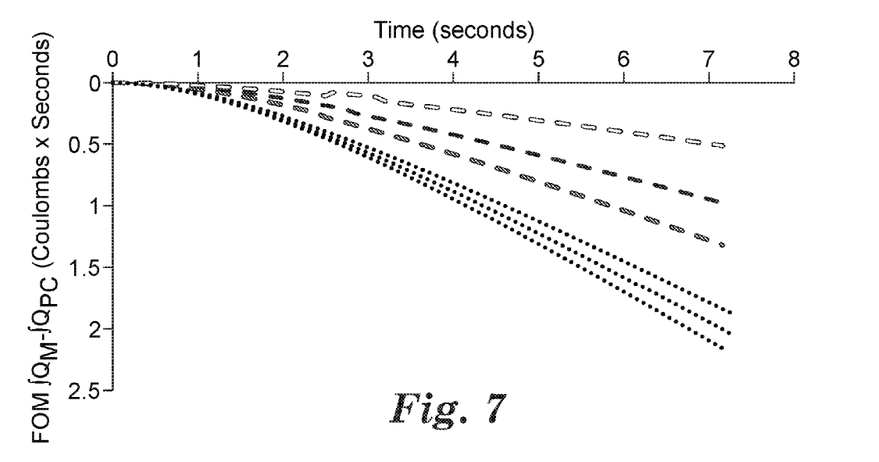
FIG. 7 is a graph of data for representative MEA samples of Example 5.

Twenty-six discrete MEA samples were prepared and tested as described for Example 1, except the figure of merit used to separate the "acceptable" and the "unacceptable" MEAs was charge difference integration ($FOM_{integration\_of\_charge\_difference}\{n\}$ in units of Coulombs*seconds) defined as:

$$FOM_{integration\_of\_charge\_difference} =$$
$$f(Q_m, Q_{PC}, T_{Q_M}, T_{Q_{PC}}) = \sum_{n=0}^{k} Q_m\{n\}\Delta T_{Q_M}\{n\} - \sum_{n=0}^{j} Q_{PC}\{n\}\Delta T_{Q_{PC}}\{n\}$$

wherein $Q_M\{n\}$ and $Q_{PC}\{n\}$ were the measured and pre-charge charge for the nth data point in the arrays, respectively, for the MEA being tested and $\Delta T_{QM}\{n\}$ and $\Delta T_{QPC}\{n\}$ is the time step for the nth sample at the measurement and pre-charge nips, respectively. Graphical representation of the $FOM_{integration\_of\_charge\_difference}\{n\}$ data for three "acceptable" (represented by dotted lines) and three "unacceptable" (represented by broken lines) MEAs are given in FIG. 7.

Example 6

Figure 8:
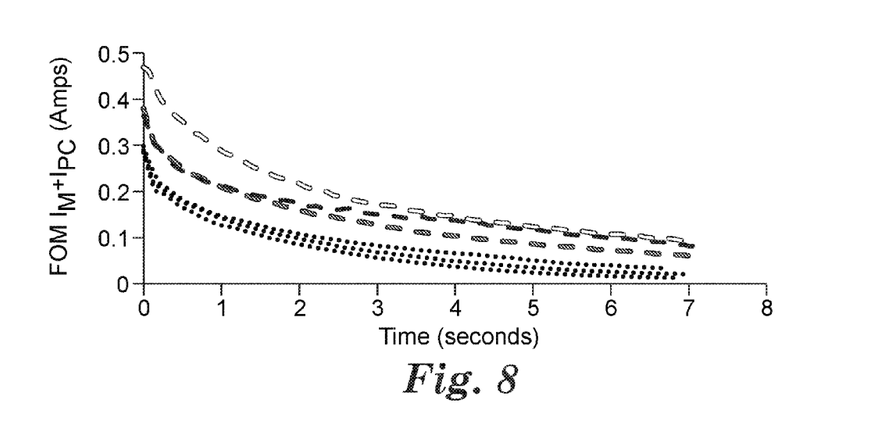
FIG. 8 is a graph of data for representative MEA samples of Example 6.

Twenty-six discrete MEA samples were prepared and tested as described for Example 1, except the voltage applied across the pre-charge and measurements nips were 0.3V and 0.25V, respectively, and the figure of merit used to separate the "acceptable" and the "unacceptable" MEAs was the sum of current comparison (FOM$_{summation\ of\ current}$\{n\} in units of amps) defined as:

$$FOM_{summation\ of\ current}\{n\}=f(I_M, I_{PC})=I_M\{n\}+I_{PC}\{n\}$$

wherein $I_M\{n\}$ and $I_{PC}\{n\}$ were the measured and pre-charge current for the nth data point in the arrays, respectively, for the MEA being tested. Graphical representation of the FOM$_{summation\ of\ current}$\{n\} data for three "acceptable" (represented by dotted lines) and three "unacceptable" (represented by broken lines) MEAs are given in FIG. 8.

Example 7

Figure 9:
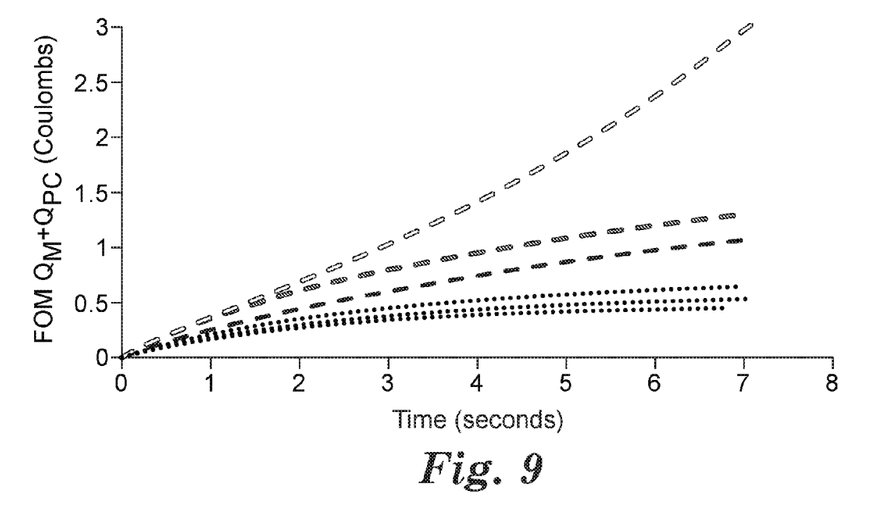
FIG. 9 is a graph of data for representative MEA samples of Example 7.

Twenty-six discrete MEA samples were prepared and tested as described for Example 6, except the figure of merit used to separate the "acceptable" and the "unacceptable" MEAs was the sum of charge comparison (FOM$_{summation\ of\ charge}$\{n\} in units of coulombs) defined as:

$$FOM_{summation\ of\ charge}\{n\}=f(Q_M, Q_{PC})=Q_M\{n\}+Q_{PC}\{n\}$$

wherein $Q_M\{n\}$ and $Q_{PC}\{n\}$ were the measured and pre-charge charge for the nth data point in the arrays, respectively, for the MEA being tested. Graphical representation of the FOM$_{summation\ of\ charge}$\{n\} data for three "acceptable" (represented by dotted lines) and three "unacceptable" (represented by broken lines) MEAs are given in FIG. 9.

Foreseeable modifications and alterations of this disclosure will be apparent to those skilled in the art without departing from the scope and spirit of this invention. This invention should not be restricted to the embodiments that are set forth in this application for illustrative purposes.

What is claimed is:

1. An apparatus comprising:
  first and second aligned roller pairs each having a nip between the aligned rollers of each aligned roller pair, wherein each of the first and second roller pairs have parallel axes of rotation, wherein each of the first and second aligned roller pairs is configured to electrically excite a portion of the web passed through the nip and to measure an electrical property of the excited web, wherein the first and second aligned roller pairs are configured to electrically excite a portion of the web passed through their respective nips are configured to provide a line of charge parallel to the axes of rotation of the respective roller pairs, and wherein the rollers of the aligned roller pairs are each electrically insulated from each other and from the apparatus; and
  a processing unit configured to at least analyze the measured electrical properties.

2. The apparatus of claim 1, wherein the electrical property measured is an array of values.

3. The apparatus of claim 1, wherein the electrical property measured is at least one of voltage or current.

4. The apparatus of claim 1, wherein the line of charge parallel to the axes of rotation of the respective aligned roller pairs independently have a length of at least 15 cm.

5. The apparatus of claim 1, wherein the electrical property measured is voltage.

6. The apparatus of claim 1, wherein the electrical property measured is current.

* * * * *

UNITED STATES PATENT AND TRADEMARK OFFICE
CERTIFICATE OF CORRECTION

| | |
|---|---|
| PATENT NO. | : 9,829,453 B2 |
| APPLICATION NO. | : 15/483660 |
| DATED | : November 28, 2017 |
| INVENTOR(S) | : Orlin Knudson |

It is certified that error appears in the above-identified patent and that said Letters Patent is hereby corrected as shown below:

In the Specification

Column 2
Line 4, delete "electrodeassembly" and insert -- electrode assembly --, therefor.

Signed and Sealed this
Twenty-sixth Day of June, 2018

Andrei Iancu
*Director of the United States Patent and Trademark Office*